(12) United States Patent
McNulty et al.

(10) Patent No.: US 8,900,821 B2
(45) Date of Patent: *Dec. 2, 2014

(54) IDENTIFICATION OF TISSUE FOR DEBRIDEMENT

(71) Applicant: KCI Licensing, Inc., San Antonio, TX (US)

(72) Inventors: Amy K. McNulty, San Antonio, TX (US); Kristine Kieswetter, San Antonio, TX (US); Todd Matthew Fruchterman, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/869,433

(22) Filed: Apr. 24, 2013

(65) Prior Publication Data

US 2013/0245386 A1     Sep. 19, 2013

Related U.S. Application Data

(63) Continuation of application No. 13/492,182, filed on Jun. 8, 2012, now Pat. No. 8,435,750, which is a continuation of application No. 13/231,251, filed on Sep. 13, 2011, now Pat. No. 8,221,989, which is a continuation of application No. 12/265,566, filed on Nov. 5, 2008, now Pat. No. 8,034,573.

(60) Provisional application No. 61/002,547, filed on Nov. 8, 2007, provisional application No. 61/002,107, filed on Nov. 5, 2007.

(51) Int. Cl.
| | |
|---|---|
| *G01N 33/53* | (2006.01) |
| *A61K 49/00* | (2006.01) |
| *G01N 33/52* | (2006.01) |
| *G01N 33/569* | (2006.01) |

(52) U.S. Cl.
CPC ........... *A61K 49/0006* (2013.01); *G01N 33/52* (2013.01); *G01N 33/56966* (2013.01); *G01N 2510/00* (2013.01)
USPC ........................................... 435/7.1; 435/7.2

(58) Field of Classification Search
None
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

Patey et al. (British J Surgery 1944 vol. 32, p. 32-35).*

(Continued)

*Primary Examiner* — Jacob Cheu

(57) ABSTRACT

Provided are methods of determining whether a cell in a tissue site is viable or nonviable. Also provided are methods of debriding tissue from a tissue site. Further provided are kits comprising a compound that distinguishes between viable and nonviable cells and instructions for using the compound on a tissue site. Additionally, the use of a compound that distinguishes between viable and nonviable cells is provided, where the use is to determine whether a cell in a tissue site is viable or nonviable. Also provided is a use of a compound that distinguishes between viable and nonviable cells, where the use is for the manufacture of the above-described kit.

13 Claims, 1 Drawing Sheet

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,497,770 A | 3/1996 | Morcos et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,528,309 B2 * | 3/2003 | Levine ..................... 435/374 |
| 6,553,998 B2 | 4/2003 | Heaton et al. | |
| 6,814,079 B2 | 11/2004 | Heaton et al. | |
| 7,960,359 B2 * | 6/2011 | Brown et al. ............. 514/44 R |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2007/0218457 A1 | 9/2007 | McKim | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 2006/102716 A1 | 10/2006 |

OTHER PUBLICATIONS

Chu et al. (Biomaterials 1995 vol. 16, p. 1381-1384).*
Yang et al. (Cell transplantation 1998 vol. 7, p. 443-451).*
Yin et al. J. of Cell Science 2007 vol. 120, p. 815-825.*
Ishii et al. J. of Immunology 2001 vol. 167, p. 2602-2607.*
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wound"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, p. 24.
Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246, 1988.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
Scaffidi Paola et al: "Release of chromatin protein HMGB1 by necrotic cells triggers inflammation", Nature, vol. 418, No. 6894, (Jul. 11, 2002), pp. 191-195, XP002261326.

* cited by examiner

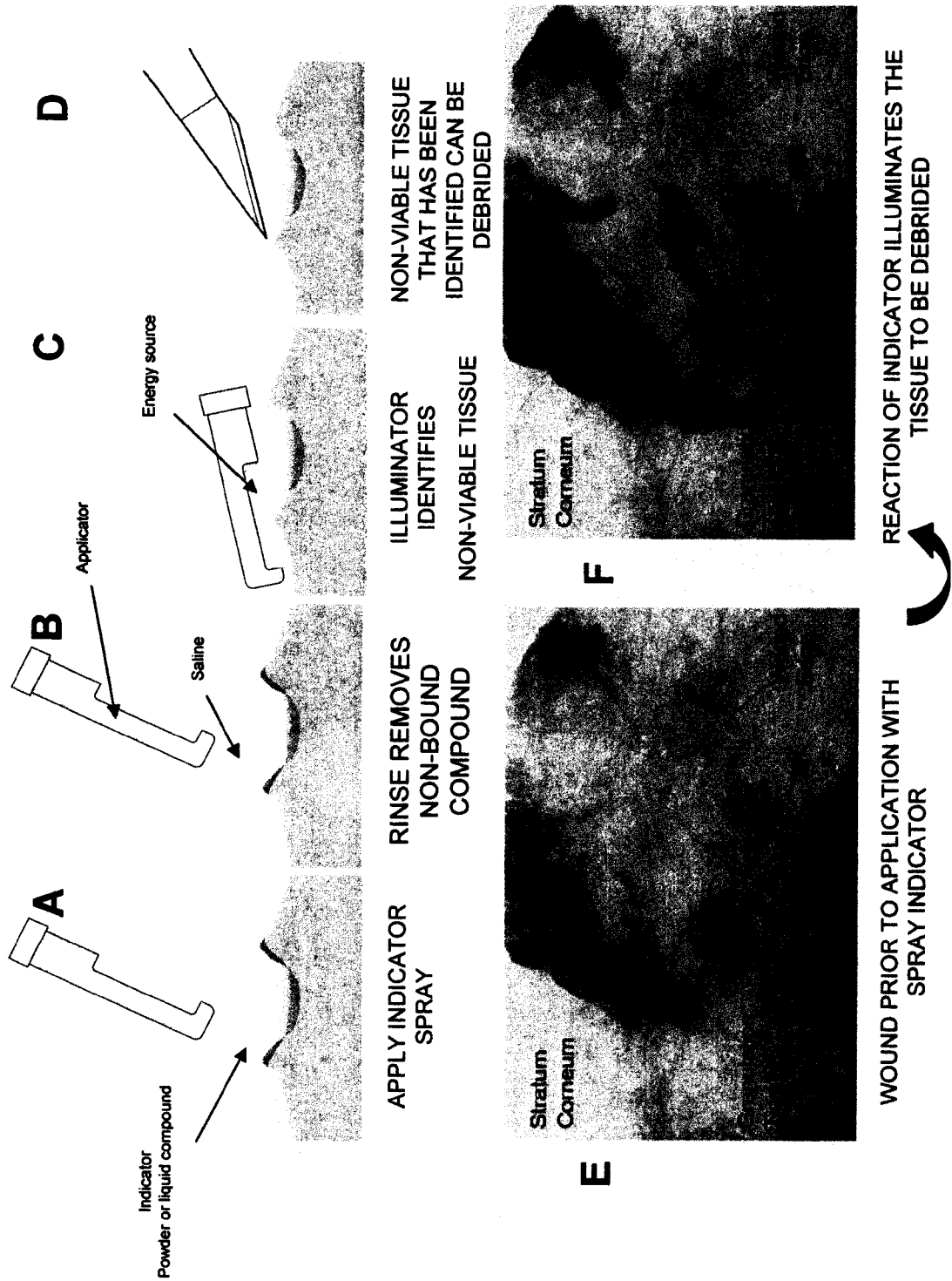

IDENTIFICATION OF TISSUE FOR DEBRIDEMENT

CROSS-REFERENCE TO RELATED APPLICATIONS

This application is a continuation of U.S. patent application Ser. No. 13/492,182 filed Jun. 8, 2012, which is a continuation of U.S. patent application Ser. No. 13/231,251 filed Sep. 13, 2011, which is a continuation of U.S. patent application Ser. No. 12/265,566, filed Nov. 5, 2008 which claims the benefit of U.S. Provisional Application No. 61/002,547, filed Nov. 8, 2007, and U.S. Provisional Application No. 61/002,107, filed Nov. 5, 2007, both of which are incorporated by reference in their entirety.

BACKGROUND

1. Field of the Invention

The present invention relates generally to tissue treatment systems and in particular to methods of determining viability of cells in vivo.

2. Description of Related Art

Wounds, however created, require aggressive debridement in order to satisfactorily remove any foreign or infectious material. Other detritus and necrotic tissue must also be removed in order to insure successful progression along the wound healing pathway. Early identification of viable vs. non-viable tissue would be useful to both the surgeon and the patient. Not only would it keep the patient from enduring additional, painful surgery, but it may also help with treatment outcomes (i.e. reducing the severity of cases, preventing removal of viable tissue and enhancing functionality). Also, identification of non-viable tissue would provide a higher level of confidence that the correct tissue was being removed and the right amount of tissue was being removed. Proper identification of tissue as non-viable would mean that one was less likely to leave visually marginal tissue.

In the case of burns, large traumatic wounds, and some chronic wounds, there exist multiple zones of tissue damage. For example, in traumatic muscle injuries, injury may cause irreversible atrophy of the muscle. In such cases, free muscle transfers may be performed to restore some function. In certain cases, it may take up to a year to determine that the muscle is non-viable and surgery is required. It is known that early treatment (muscle transfer) may lead to better outcomes, and that delay in treatment limits the reconstruction options (Barrie et al., 2004). On the other hand, the more healthy tissue that remains following debridement, the better the outcome. Identification of viable tissues would prevent inadvertent removal of viable tissue.

The differential levels of tissue damage are perhaps most classically described as the "Jackson zones" identified in burns (Jackson, 1953). The most severely and irreversibly damaged area is known as the zone of coagulation due to the destruction of the local proteins. This area is clearly unsalvageable. It is necrotic, often blackened and charred, and must be removed. The most peripheral and least damaged area is known as the zone of hyperemia. Tissue in this region generally completely recovers from the trauma unless it becomes infected or suffers prolonged hypoperfusion.

Tissue in the intermediate zone of stasis has been injured and is potentially salvageable. This is known as the zone of stasis. In mid to deep burn injuries, these wounds can not be salvaged or convert to the zone of necrosis. As reported by Molnar et al. (2005), "This is characterized by increased vascular permeability, edema, and progressive blood viscosity, leading to thrombosis and additional tissue death. It is this zone of stasis that represents the deep second-degree burn that is clearly viable tissue when the patient arrives but subsequently goes on to die and requires excision and grafting much in the manner of a third-degree or full-thickness burn." When this occurs, wound healing is impeded, and the patient may have to go back in for additional, painful, debridement.

As stated above, the viability of the tissue is dependent upon the ability of the cells in this area to recover from the physiological insults arising from the burns. If the cells are able to receive adequate perfusion and nutrients in a timely fashion, the tissue may survive. If on the other hand, this does not occur, as edema increases, perfusion decreases, tissue oxygenation decreases and the injury progresses resulting in cell and tissue death over the 48-72 hours post-injury. Similar zones of injury, albeit not as visually striking, occur in traumatic wounds, as well as chronic wounds such as decubitus, to various tissues.

The Faustian quandary for the surgeon is whether to (1) conservatively debride, allowing some of the marginal tissue to stay in place and weighing the balance between whether the tissue will respond to the resuscitation efforts or whether the tissue will succumb, become necrotic, provide a nidus for infection and have to be removed at a subsequent procedure or (2) aggressively debride well beyond the margin of the clearly injured tissue, potentially removing viable or recoverable tissue, and by taking this wide swath of tissue severally limiting options for future reconstructive options and hence, functionality.

Currently, debridement and tissue removal in traumatic injuries generally depends upon the surgeon's knowledge of viable tissue morphology. However, in many instances this is not 100% accurate. Areas may look questionable, and it is not until later that it is determined that the tissue is nonviable. At this point, another trip back to the operating room, and another painful debridement is warranted. Conversely, traumatic injuries may be treated by aggressive tissue removal. Tissue which may be viable or recoverable may be removed, limiting future functionality.

Thus, in wound healing, repeated surgical debridement procedures can be required. If senescent or non-viable cells are left at the wound edge, the wound may fail to progress towards healing. A need therefore exists for a method that provides clear identification of the areas of the tissue that have exhibited clear markers of having succumbed to the injury. The surgeon will then know which areas should be excised at the time of the debridement and which should be allowed to remain so that the tissue can recover from the insult and serve as a platform for any reconstruction that may be required in the future.

Efforts to identify senescent tissue in vivo include those of US 2007/0197895 A1, describing an instrument that emits and receives acoustic signals. Also, WO07/130,423A2, describes methods for identifying a margin for debridement by obtaining tissue samples from the tissue site and evaluating expression profiles of the samples, where tissue from within a wound has a different gene expression profile from tissue adjacent to a wound.

There is a need for additional methods that allow a precise and unambiguous continuous identification of viable and nonviable cells in a timely manner, e.g., on the edge of wounds, to determine where debridement should take place. The present application addresses that need.

SUMMARY

Problems presented by existing methods of surgical debridement are solved by the systems and methods of the illustrative embodiments described herein. In one embodiment, a method of determining whether a cell in a tissue site is viable or nonviable is provided that comprises adding a compound that distinguishes between viable and nonviable cells to the tissue site, then determining whether the compound indicates that the cell is viable or nonviable.

In another embodiment, a method of debriding tissue from a tissue site comprising viable and nonviable tissue is provided that comprises adding a compound that distinguishes between viable and nonviable tissue to the tissue site, then determining where viable and nonviable tissue is in the tissue site, then debriding the nonviable tissue surgically.

Also provided is a method of determining whether a cell in a tissue site is viable or nonviable. The method comprises visualizing the tissue under conditions where a viable cell can be distinguished from a nonviable cell.

In an additional embodiment, a kit is provided that comprises a compound that distinguishes between viable and nonviable cells, and instructions for using the compound on a tissue site by the above-described methods.

In a further embodiment, the use of a compound that distinguishes between viable and nonviable cells is provided, where the use is to determine whether a cell in a tissue site is viable or nonviable.

Also, a further use of a compound that distinguishes between viable and nonviable cells is provided, where the use is for the manufacture of the above-described kit.

Other objects, features, and advantages of the illustrative embodiments will become apparent with reference to the drawings and detailed description that follow.

BRIEF DESCRIPTION OF THE DRAWINGS

FIG. 1 is diagrams and photographs illustrating an embodiment of the invention.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The inventors have developed methods for determining whether tissue is viable or nonviable in situ. These methods allow precise determination of which cells are viable and which are nonviable in a tissue site. Because of the precision of several embodiments of these techniques in identifying specific cells that are viable or nonviable, debridement can be more accurate in removing nonviable cells and leaving viable cells intact. Indeed, with the present methods, techniques that target individual cells or small groups of cells, such as laser dissection techniques, become more useful in debridement procedures because specific cells can be identified as viable or nonviable. Thus, with these techniques, the physician can precisely remove more nonviable tissue and leave more viable tissue intact than with currently practiced debridement procedures.

In some embodiments, the application is directed to a method of determining whether a cell in a tissue site is viable or nonviable. The method comprises adding a compound that distinguishes between viable and nonviable cells to the tissue site, then determining whether the compound indicates that the cell is viable or nonviable.

These methods and all other methods described herein can be used with any vertebrate including birds, reptiles and any mammal, including horses, cats, dogs, cows, sheep, goats, pigs and humans.

As used herein, a cell is viable if it is alive and not destined to die, e.g., by apoptosis, necrosis or senescence. "Viable cell" also includes a cell that is 'stunned' but alive, i.e., cells that sustained some damage, e.g. cells at the margin of a burn that were heated and may not function properly for a time, but would be expected to recover. Generally, a cell would be expected to recover if it has not lost its integrity. This can be measured by determining whether the cell is permeable to certain dyes, whether metabolites are leaking excessively into the surrounding tissue, whether intracellular or intraorganelle proteins (e.g., cytochrome c) or enzymes (e.g., esterases) are present outside the cell, by the various methods described herein, or any other procedure known in the art.

The compound can be formulated in any manner known in the art. The skilled artisan can determine, without undue experimentation, a useful formulation for any particular application. Useful formulations include a gel, spray, liquid, powder, cream, lotion, ointment, suspension, sheet, or other solid, semisolid or liquid which can be dusted onto, painted on, sprayed into, poured on, laid over or otherwise administered into or onto the tissue site so that it can come into contact thereto.

As used herein, a sheet is a broad, relatively thin coherent mass or piece of material, including those made from bioabsorbable or nonbioabsorbable materials, or both. Examples include pads, sponges, paper and thin membranes. The sheet can be transparent or opaque and can be in any two-dimensional shape. The compound can be covalently bound or simply adsorbed to, or absorbed into, the sheet.

Any of the compound formulations can include any other agents, including bioactive agents, e.g., an antibiotic or a growth factor. Nonlimiting examples of growth factors which could be useful in the compound formulations include a vascular endothelial growth factor (VEGF), a fibroblast growth factor (FGF), a platelet derived growth factor (PDGF), an angiogenin, an angiopoietin-1, a del-1, a follistatin, a granulocyte colony-stimulating factor (G-CSF), a hepatocyte growth factor/scatter factor (HGF/SF), an interleukin-8 (IL-8), an IL-1β, an IL-1, an IL-6, a leptin, a midkine, a placental growth factor, a platelet-derived endothelial cell growth factor (PD-ECGF), a platelet-derived growth factor-BB (PDGF-BB), a PDGF-AB, a pleiotrophin (PTN), a progranulin, a proliferin, an epidermal growth factor (EGF), a keratinocyte growth actor (KGF), an activin A, a transforming growth factor-α (TGF-α), a transforming growth factor-β (TGF-β), a tumor necrosis factor-α(TNF-α), a vascular endothelial growth factor (VEGF), a matrix metalloproteinase (MMP), an angiopoietin 1 (ang1), an ang2, and a delta-like ligand 4 (DLL4).

The compound in these methods include anything that can be used to distinguish viable from nonviable tissue. In some embodiments, the compound identifies a molecule that has a differential expression pattern in viable vs. nonviable cells. The differential expression pattern could be in quantity (e.g., a different amount of the molecule is present in, or is released by, nonviable cells vs. viable cells) or location (e.g., intercellular vs. extracellular presence of the molecule).

In some embodiments, the compound comprises an antibody binding site, e.g., an antibody, an Fab fragment, an F(ab)2 fragment, or a heterologous protein engineered to comprise an antibody binding site.

In other embodiments, the compound comprises an aptamer. Aptamers are oligonucleotides produced in vitro which are generally used to bind to specific proteins, but which may also be used to bind to cells. Aptamers can be prepared by an iterative selection process to bind specifically and tightly to most proteins or other molecules (Brody and Gold, 2000). Because of their specificity and binding abilities, aptamers are believed to have great potential as diagnostic agents (Brody and Gold, 2000; U.S. Pat. No. 7,052,854). Aptamer preparation does not require either animal or cultured cells. Aptamer synthesis may be conducted through PCR, and the resulting aptamers are stable at room temperature and have a long shelf life. Visualization of the aptamer-bound proteins may be conducted by any one of a number of different methodologies, for example as outlined in Seal et al., 2006 and Mir et al., 2007.

The compound can also comprise a small organic molecule, e.g., less than about 5000 mw, 2000 mw, 1000 mw, or 500 mw. An example is a substrate of an enzyme (e.g., isopropyl-β-D-thiogalactopyranoside [IPTG], which is converted from a colorless substrate to a colored product by β-galactosidase).

In some embodiments, the compound comprises a detectable marker, e.g., conjugated to the antibody, aptamer or small organic molecule. The detectable marker can be any known in the art, provided the marker can be detected visibly or utilizing other portions of the electromagnetic spectrum, with an instrument such as a camera, a dissecting microscope or a Geiger counter, through a filter, or after subsequent processing, such as adding an enzyme substrate to achieve a colored product. As is known in the art, a filter is particularly useful when the detectable marker is fluorescent, where the filter is used to block out excitation wavelengths while letting emission wavelengths pass through. Nonlimiting examples of detectable markers are enzymes, dyes (including visible and fluorescent dyes), radioactive compounds, quantum dot-containing compositions, and metals or metal-containing compositions (including proteins) such as ferritin or a magnetic contrast agent such as that described in WO07069040A2. The latter compounds are particularly useful for using optical coherence tomographic imaging to evaluate cell viability. See, e.g., U.S. Patent Application Publication US 2007/0038121 A1.

The detectable marker could also be introduced secondary to the application of the compound. For example, the compound could be an antibody that binds to a protein expressed in nonviable tissues but not viable tissues. To determine whether the antibody is binding to the protein, a second antibody conjugated to the detectable moiety, such as a fluorescent dye or enzyme, is added; the tissue is then washed and the detectable moiety is visualized. Where the detectable moiety is an enzyme, an enzyme substrate that forms a colored product is added to visualize its presence. Alternatively, if the compound is an antibody incorporated into a sheet, and the compound binds to a protein that is released from nonviable cells, the sheet may be laid onto the tissue site allowing the protein to bind, then a second antibody that binds to the protein is added to the sheet, where the second antibody further comprises a detectable label, forming an antibody-protein-antibody* "sandwich". The detectable label (*) is then visualized. Such an assay can be performed with the sheet in situ. Alternatively, the sheet can be removed from the tissue site and further processed to add the labeled second antibody and visualize the label.

In one embodiment, the compound could comprise inert, biocompatible particles such as carbon black or colloidal gold bound to it, or bound to a quantum dot or use up-converting phosphor technology (UPT).

The compound, or detectable label thereon, may also be light activated to distinguish between viable and nonviable cells. See, e.g., U.S. Pat. No. 6,057,096.

In some embodiments of these methods, the compound is a dye. Included are viability dyes, for example a dye that is more visible or fluorescent in viable cells than in nonviable cells. Nonlimiting examples include fluorescein diacetate, trypan blue, and calcein AM. See also http://probes.invitrogen.com/handbook/print.1502.html.

In one aspect of these embodiments, the compound is a dye that shows reactive oxygen species concentrations. Cells which are healthy can produce reactive oxygen species concentrations. For example, dihydrorhodamine 123 is a hydroperoxide sensitive fluorescent probe. In viable cells it is trapped in a non-fluorescent form. However, it is converted to the mitochondrial selective form, rhodamine 123 by hydroperoxide. Light emission from rhodamine 123 may be recorded by digital microscopy.

In other embodiments, the dye is more visible or fluorescent in nonviable cells than in viable cells. Included here are dyes that cross the nuclear membrane of only nonviable cells. Examples are propidium iodide and ethidium bromide.

A dye that indicates mitochondrial death can also be used as a viability dye. Actively metabolizing mitochondria are characterized by high inner membrane potential. This dissipates in cells about to undergo apoptosis or necrosis. Mitochondrial activity may be visualized by JC-1 dye accumulation. This dye exhibits a diffuse green fluorescence in the cytoplasm of dead mitochondria and is viewed as red fluorescence when mitochondria are active.

An alternate embodiment includes incorporation of a biocompatible dye into a liposome covered with the proteins that bind to the compound. Once the two components are bound to each other and the tissue site is cleaned of the formulation, the dye can be released from the liposomes via directed energy such as ultrasonic stimulation or other appropriate energy input.

Piezoelectric crystals capable of emitting energy in an appropriate format for eliciting visualization is also consistent with this invention.

The compound can identify a molecule, for example a protein (e.g., enzyme, electron transport protein, structural protein, membrane protein), nucleic acid (e.g., genomic or mitochondrial DNA, an RNA), carbohydrate (e.g., polysaccharide), lipid, or small molecule (e.g., a metabolite), provided the molecule has a differential expression pattern in viable vs. nonviable cells. As discussed above, the differential expression pattern could be in quantity or location. The molecule could also have a different structure in viable vs. nonviable cells, e.g., a protein may be denatured in nonviable cells but not in viable cells.

In some embodiments, the compound identifies a protein. The protein identified by the compound may be elevated during the process of cell death, e.g., during apoptosis, senescence or cell necrosis. For example, the protein may be elevated inside dead or dying cells. Alternatively or additionally, more of the protein may be released from dead or dying cells than from viable cells. As used herein, a protein released from a cell moves from inside to outside the cell. The release can be by an active cellular process and/or by passive leaking out of the cell, e.g., due to increased permeability of the cell or an organelle of the cell, such as mitochondria.

Where the protein identified by the compound is released from dead or dying (i.e., nonviable) cells, the presence of the compound outside the nonviable cells may be determined by placing a sheet comprising the compound on the tissue site, where the compound is capable of binding or reacting to the released protein on the tissue site, then determining whether the protein is bound or has reacted to the compound. In these embodiments, areas of the sheet comprising protein bound to the compound are nonviable tissue. The tissue site may then be debrided adjacent to areas of the sheet indicating nonviable tissue. After assaying for nonviable tissue using the sheet of these embodiments, the sheet, or a portion thereof, can be removed, providing a 'map' of the viable and nonviable areas of the tissue site. Such a removed sheet can be stored in the patient's records. At least a portion of the sheet can also remain on the tissue site, e.g., as a guide for debridement. The sheet can further comprise a bioactive agent, for example an antibiotic or growth factor. Where present, the bioactive agent could prevent infection or stimulate wound healing, particularly when the sheet is left on the tissue site, e.g., after debridement.

The sheet of these embodiments can be made of bioabsorbable or non-biodegradable material, or both. When the sheet is to remain on the tissue site, a bioabsorbable sheet is often preferred. Nonlimiting examples of materials that could be used in the sheets are starch films, collagen, nitrocellulose, regenerated cellulose, a cellulose acetate, acyl substituted cellulose acetates and derivatives thereof including ethylene-vinyl acetate polymers, polyvinylidene fluoride (PVDF), collagen, polyvinyl alcohol, poly(D,L-lactide-co-glycolide), polyglycolic acid, poly-(L-lactic acid), polyanhydrides, polysaccharides (e.g. alginate), polyphosphazenes, polyacrylates, polyethylene oxide-polypropylene glycol block copolymer, poly(caprolactone), polycarbonates, polyamides, polyanhydrides, polyamino acids, polyorthoesters, polyacetals, polycyanoacrylates, degradable polyurethanes, polyacrylates, polyhydroxyalkanoates including polyhydroxybutyrates and polyhydroxyvalerates, polyurethanes, polystyrenes, polyvinyl chloride, polyvinyl fluoride, poly(vinylimidazole), chlorosulphonated polyolefins, polyethylene oxide, polyvinyl alcohol, Teflon®, and nylon. In some embodiments, the sheet is a starch film, a poly(D,L-lactide-co-glycolide), a polyglycolic acid, a poly-(L-lactic acid) or a polyhydroxyalkanoate. The skilled artisan could, without undue experimentation, determine and obtain a sheet suitable for any particular embodiment of the application methods.

The compound in the sheet that identifies the protein released by nonviable cells can be a protein (e.g., an antibody), a nucleic acid (e.g., an aptamer), a small organic molecule (e.g., an enzyme substrate), a dye, or any other compound that specifically binds to the protein, as discussed above. The compound can further be conjugated to a detectable marker (e.g., a dye, an enzyme capable of catalyzing the conversion of a colorless substrate into a colored product, a radioactive moiety, etc.), as discussed above. In some embodiments, the released protein is an enzyme and the compound is a substrate of the enzyme.

In some embodiments, the protein identified by the compound is elevated in a cell undergoing apoptosis. In other embodiments, the protein is elevated during cell necrosis or senescence. As is known in the art, apoptosis is an active process characterized by cell shrinkage, generally without an inflammatory response. Apoptotic cells are usually identified using an assay involving terminal deoxynucleotidyl transferase dUTP nick end labeling, or the TUNEL assay, which detects DNA fragmenting that is characteristic of apoptosis. By contrast, necrosis is a passive process generally involving cell swelling and an inflammatory response. Senescence is characterized by giant cells that metabolize but do not proliferate. It is usually induced by telomere shortening, P21 expression or γ-irradiation.

Nonlimiting examples of proteins that are elevated in the cell or outside the cell in cell death and may be detected by the compound are cytochrome c, second mitochondria-derived activator of caspases (Smac), β-galactosidase, lipofuscin, HMGB1, NF-κB, glyceraldehyde 3-phosphate dehydrogenase, a protein with an advanced glycation end product (AGE), vimentin, lamin A, creatine kinase, peroxiredoxin 1, soluble galactose-binding lectin 7, and collagen. In some embodiments, the protein is β-galactosidase, lipofuscin, an AGE, cytochrome c, lamin A, creatine kinase, peroxiredoxin 1, soluble galactose-binding lectin 7, or collagen.

β-galactosidase and lipofuscin are two proteins that identify senescent cells (Gerland et al., 2003). HMGB1 is a chromatin binding protein that is associated with both apoptosis and necrosis. In apoptotic cells, HMGB1 is immobilized and does not increase the inflammatory response. However, in necrotic cells, HMGB1 is released from the nuclei in massive amounts and may initiate further cell death and organ necrosis (Bustin, 2001; Scaffidi, 2002). Increases in NF-κB may lead to muscle wasting. Additionally, elevated AGE levels in proteins can indicate cell death. See Van Herreweghe et al., 2002. AGE are particularly common in diabetes and would thus be a particularly useful target to determine cell death in a diabetic animal. Example 1 establishes that lamin A, creatine kinase, peroxiredoxin, a galactose-binding lectin, collagen, and filaggrin, among other proteins, are increased in dying tissue.

A structural protein such as vimentin may be the protein identified by the compound. Vimentin becomes externalized as cells proceed toward death. The presence of vimentin, or other proteins that are externalized upon cell death, would indicate a non-viable tissue.

In other embodiments, the protein identified by the compound is depleted during cell death. Nonlimiting examples are γ-actin, biglycan, complement component 3, fibronectin 1, $\alpha_1$ proteinase inhibitor, serine protease inhibitor 2b, transferrin, apolipoprotein A-1, pregnancy-zone protein, and hemoglobin (both α and β chains). Muscle cell death may occur if γ-actin is absent. Another example is biglycan (Schaefer et al., 2003). The inventors have discovered that biglycan is depleted during cell death. Additionally, Example 1 describes the reduction of complement component 3, fibronectin 1, $\alpha_1$ proteinase inhibitor, serine protease inhibitor 2b, transferrin, apolipoprotein A-1, pregnancy-zone protein, and hemoglobin in dying cells.

In another embodiment, the mitochondrial membrane potential may be determined. Since cells that are dead or dying do not have intact mitochondrial membranes, a difference would be indicated by the mitochondrial membrane potential of live, healthy cells. A compound that is useful for this purpose is the dye JC-1, as discussed above.

In additional embodiments, the compound specifically binds to a denatured protein that is present in nonviable tissues more than in viable tissues. Nonviable cells frequently accumulate denatured proteins. These can be detected with, e.g., an aptamer or antibody that specifically binds to the denatured form of a protein but not the nondenatured form. With these embodiments, the denatured form of any protein can be evaluated. In some embodiments, the denatured protein is collagen, which is abundant. Antibodies to denatured collagen are commercially available.

The compound of these methods can, in some embodiments, detect naked DNA that has been released from a necrotic or apoptotic cell. Naked DNA can be detected using, e.g., dyes that bind to DNA, such as ethidium bromide.

In other embodiments, the compound identifies an organic molecule less than about 5000 mw, or less than about 2000 mw, or less than about 1000 mw, or less than about 500 mw. The organic molecule can be, for example, a metabolite that is released from nonviable cells more than from viable cells. Nonlimiting examples of such metabolites are ATP, glucose, glycerol, NADPH and NADH. The compound can be a component of a known assay for the metabolite, for example luciferase or luciferin for ATP; glucose oxidase, peroxidase or a peroxidase substrate for glucose; glycerol kinase, glycerol phosphate oxidase, peroxidase or a peroxidase substrate for glycerol; alcohol dehydrogenase, a tetrazolium dye, or phenazine methosulfate for NADH; and glucose dehydrogenase, phenazine methosulfate, or a tetrazolium dye for NADPH. It is contemplated that more than one compound can be added to the tissue site, for example, if the metabolite is NADH, alcohol dehydrogenase, a tetrazolium dye, and phenazine methosulfate can all be added to the tissue site, in order to effect identification of NADH on the tissue.

With these metabolites, the method can further comprise placing a solid sheet comprising the compound on the wound, where the compound binds or reacts with the organic molecule on the wound, then determining whether the organic molecule is bound or has reacted to the compound. In these methods, any areas of the sheet comprising the organic molecule bound to the compound is nonviable tissue.

These methods can be used to determine viability of any type of mammalian cell present in any tissue site. Nonlimiting examples include epidermal cells, dermal cells, fibroblasts, mesenchymal stem cells, osteoblasts, chondrocytes, myocytes, adipocytes, endothelial cells, vascular smooth muscle cells and neuronal cells.

While these methods are designed to be used on wounds, they can be used to determine tissue viability in any tissue site including normal tissue or diseased tissue (e.g., necrotizing fasciitis). The methods can also be used in internal organs, e.g., prior to pancreatic necrosectomy (Parekh, 2006) or nasal sinus debridement.

The tissue site evaluated by these methods can be anywhere on or in a mammal where determination of cell viability in situ is desired, e.g., where debridement is planned. Tissue types that can be utilized include epithelium, connective tissue, muscle tissue, pancreatic tissue and neural tissue.

These methods can be used on any tissue site. In some embodiments, the tissue site is a wound. The methods can be used on any wound where there is a possibility of the presence of nonviable tissue. The wound may be from, e.g., a burn, disease or trauma.

In many embodiments, the nonviable tissue identified by these methods are selectively debrided. In some of these embodiments, the nonviable tissue is debrided with a sharp instrument, ultrasound or a hydrojet, as they are known in the art. In other embodiments, the nonviable tissue is debrided with a laser. Due to the accuracy of these methods in identifying individual viable and nonviable cells, debridement with a laser is useful to eliminate nonviable cells and retain viable cells.

The application is also directed to a method of debriding tissue from a tissue site comprising viable and nonviable tissue. The method comprises adding a compound that distinguishes between viable and nonviable tissue to the tissue site, then determining where viable and nonviable tissue is in the tissue site, then debriding the nonviable tissue surgically.

In some embodiments, the tissue site is a wound. The methods can be used on any wound where there is a possibility of the presence of nonviable tissue. The wound may be from, e.g., a burn, disease or trauma.

As with the methods described above, the compound can be selected to identify a protein elevated in cell death. Alternatively, the compound can be selected to identify a protein that is depleted during cell death.

In some embodiments, the compound comprises an antibody binding site. In other embodiments, the compound is an aptamer. In still other embodiments, the compound is a dye.

In some of these embodiments, the nonviable tissue is debrided with a sharp instrument, ultrasound or a hydrojet. In other embodiments, the nonviable tissue is debrided with a laser.

There are also various optical methods available that allow direct visualization of viable or nonviable tissue without prior addition of a compound. Thus, the application is also directed to a method of determining whether a cell in a tissue site is viable or nonviable. The method comprises visualizing the tissue under conditions where a viable cell can be distinguished from a nonviable cell.

In some embodiments, the tissue is visualized using optical coherence tomography. Such methods are useful for determining the condition of tissue. See, e.g., Todorovic et al., 2008. In other embodiments, the tissue is visualized using interferometry. See, e.g., Schneider et al., 1997.

In additional embodiments of this method, autofluorescence is visualized under conditions where tissue having high levels of autofluorescence are viable and tissue having low levels of autofluorescence are nonviable. See, e.g., U.S. Pat. No. 6,174,291. In one aspect, NADH and NADPH levels are evaluated with these embodiments, since autofluorescence of these compounds decline preceding apoptosis (Toms et al., 2005). Where autofluorescence of NADH and NADPH are evaluated, autofluorescence can be visualized at about 460 nm with excitation at about 355 nm.

In other embodiments, the method further comprises imaging the tissue site through a multispectral or hyperspectral camera, where the camera images spectra distinguishing viable and nonviable cells. Multispectral scanning has been used to determine various characteristics of tissue, including viability. See U.S. Provisional Patent Application Publication 2008/0192248A1 and U.S. Pat. No. 7,366,365.

Further, multispectral and hyperspectral technology are useful for identifying molecules with spectral properties. With hyperspectral and multispectral imaging for these methods, the imaged spectra can distinguish a molecule with spectral properties in a viable cell from the molecule in or released from a nonviable cell. Molecules such as hemoglobin and cytochromes have spectral properties. Thus, in some embodiments the molecule is a cytochrome or a hemoglobin, e.g., cytochrome c. The hyperspectral technology can identify mitochondria with reduced versus oxidized cytochrome c, or where cytochrome c has escaped into the cytoplasm, thereby identifying apoptotic cells.

These methods can be used on any tissue site. In some embodiments, the tissue site is a wound. The methods can be used on any wound where there is a possibility of the presence of nonviable tissue. The wound may be from, e.g., a burn, disease or trauma.

In many embodiments, the nonviable tissue identified by these methods are selectively debrided. In some of these embodiments, the nonviable tissue is debrided with a sharp instrument, ultrasound or a hydrojet. In other embodiments, the nonviable tissue is debrided with a laser.

The application is also directed to a kit. The kit comprises a compound that distinguishes between viable and nonviable cells and instructions for using the compound on a tissue site by any of the methods described above. The methods comprise adding a compound that distinguishes between viable and nonviable cells to the tissue site, then determining whether the compound indicates that the cell is viable or nonviable.

The various methods for determining whether a cell in a tissue is viable can be used in vitro to determine the viability of cells in tissue engineering construct, e.g., for quality control. Using these methods, unsuitable areas can be resected prior to implantation, eliminating undesirable responses, such as inflammatory responses, to the nonviable tissue and increasing the potential for the construct's success.

Thus, in additional embodiments, the application is directed to a method of determining the viability of a cell in a tissue engineering construct comprising cells. The method comprises adding a compound that distinguishes between viable and nonviable cells to the tissue engineering construct, then determining whether the compound indicates that the cell is viable or nonviable.

In some aspects of this method, the compound identifies a protein that is elevated in cell death. In other aspects, the compound identifies a protein that is depleted in cell death. In additional aspects, the compound identifies an organic molecule less than about 2000 mw. In further aspects, the compound is a dye. The various compounds for these methods are as described above. In some aspects, the method further comprises removing nonviable cells from the tissue engineering construct.

In further embodiments, the application is directed to a method of determining the viability of a cell in a tissue engineering construct comprising cells. The method comprises visualizing the tissue under conditions where a viable cell can be distinguished from a nonviable cell. As with the analogous methods described above, the tissue can be visualized, e.g., using optical coherence tomography, interferometry, visualization of autofluorescence, or a multispectral or hyperspectral camera. In some aspects, the method further comprises removing nonviable cells from the tissue engineering construct.

The application is additionally directed to the use of a compound that distinguishes between viable and nonviable cells to determine whether a cell in a tissue site is viable or nonviable. In some embodiments, the cell in the tissue site is debrided if it is nonviable. In further embodiments, the tissue site is a wound. The methods can be used on any wound where there is a possibility of the presence of nonviable tissue. The wound may be from, e.g., a burn, disease or trauma.

Further, the application is directed to the use of a compound that distinguishes between viable and nonviable cells for the manufacture of a kit. The kit comprises a compound that distinguishes between viable and nonviable cells and instructions for using the compound on a tissue site by any of the methods described above.

The application is also directed to the use of a compound that distinguishes between viable and nonviable cells to determine the viability of a cell in a tissue engineering construct.

It is recognized that more than one of the above methods and uses may be combined to increase the accuracy of the determination of the boundaries of viable and non-viable tissue, and/or to have an internal check on the accuracy of each assay. For example the above methods of using a compound that identifies β-galactosidase could be combined with the multispectral or hyperspectral methods described above.

FIG. 1 provides an illustration of one embodiment of the invention. In this embodiment, the tissue site is sprayed with an indicator spray of a powder or liquid comprising a compound as described above (Panel A). Examples of compounds that can be applied here include viability dyes or antibodies labeled with, e.g., a fluorescent dye. The tissue site is then rinsed to remove compound that is not bound to the tissue (Panel B). The tissue is then illuminated, e.g., with light of the dye excitation wavelength (Panel C). The tissue identified here as nonviable is then debrided (Panel D). An illustration of what tissue before and after treatment with the compound could look like is provided in Panels E and F.

Preferred embodiments are described in the following example. Other embodiments within the scope of the claims herein will be apparent to one skilled in the art from consideration of the specification or practice of the invention as disclosed herein. It is intended that the specification, together with the example, be considered exemplary only, with the scope and spirit of the invention being indicated by the claims, which follow the example.

EXAMPLE 1

Changes in Protein Concentrations in Injured or Dying Tissue

The following experiment was conducted to identify proteins that are increased or decreased in injured or dying cells.

Thermal injuries were produced on the backs of rats (*Rattus norvegicus*) as follows. The open barrel of a 3 cc syringe was placed against the skin and filled with 60° C. water. This was left in contact with the skin for 30s, at the end of which ice water was added to cool the syringe to room temperature. Following syringe removal, silvadene cream was topically applied to all wounds. Wounds were removed at necropsy, at either 4 hours or 5 days.

Tissue was divided into 1 cm pieces from the zone of necrosis. This corresponds to the different Jackson Zones. Therefore the pieces should have been dead at the center, the piece 2 cm from the center should have been viable and the intermediate zone should have shown some sign of injury.

Tissue was extracted for proteins and labeled using stable isotopic labeling (iTRAQ, ABI). Protein extraction was by acetone precipitation from up to eight tissue types with each isolate being reduced, cysteine-blocked, digested with trypsin and subsequently given a unique label. Once all samples were individually labeled, they were combined to make one mixture with each label identifying the unique protein source. To clean up the sample of any impurities such as salt build-up (a common occurrence that can impact MS evaluation) and also fractionate the mixture, strong cation-exchange (SCX) chromatography was utilized by running the mixed sample through HPLC utilizing a PolyLC column which separated the digest into fractions by differences in charge-to-mass ratio. The collected fractions were then utilized for spotting onto the excitation plate prior to its introduction to the mass spectrometer.

Information based on the "time of flight" and the peptide labeling "fingerprint," was gathered and inputted into a protein database (in this case Mascot) for peptide identification and matching of other fragments. This allowed for quantification of peptide levels in comparison between normal and injured tissue. Therefore the final output was a determination of proteins which were either up or downregulated between injured and normal tissues.

Results are provided in Table 1. "Accession" refers to a Genbank accession number. Numbers lower than 1 in the 115:113 column indicate a reduced amount of the indicated protein in necrotic tissue; numbers greater than 1 indicate an increased amount of the indicated protein in necrotic tissue. Necrotic tissue had less hemoglobin (both α2 chain and β chain), complement component 2, pregnancy-zone protein, fibronectin 1, alpha-1-inhibitor III ($\alpha_1$ proteinase inhibitor), serine protease inhibitor 2b, apolipoprotein A-1 and transferrin than viable tissue. Necrotic tissue also had more lamin A, creatine kinase, peroxiredoxin 1, soluble galactose binding lection, parvalbumin, collagen, and other proteins than viable tissue.

Scaffidi, P., Misteli, T., Bianchi, M. E. Release of chromatin protein HMGB1 by necrotic cells triggers inflammation. Nature. 418, 2002. p 191-195.

Schaefer, L. et al. J. Biol. Chem. 278, 2003. p. 26227-26237.

Schneider, B. H. et al. Clin. Chem. 43, 1997. p. 1757-1763.

Seal, J., Braven, H., Wallace, P., "Point-of-care nucleic acid lateral-flow tests," IVD Technology, 12(9), 2006. p 41-51.

Todorovic, M. et al. Optics Express. 16, 2008. p. 10279-10284.

TABLE 1

| Accession | Name | 115:113 | PVal 115:113 |
|---|---|---|---|
| gi\|60678292 | hemoglobin alpha 2 chain [Rattus norvegicus] | 0.4329 | 2.6685E−08 |
| gi\|17985949 | hemoglobin beta chain complex [Rattus norvegicus] | 0.4639 | 0.00251685 |
| gi\|158138561 | complement component 3 [Rattus norvegicus] | 0.5344 | 2.8278E−07 |
| gi\|21955142 | pregnancy-zone protein [Rattus norvegicus] | 0.5928 | 1.4014E−05 |
| gi\|9506703 | fibronectin 1 [Rattus norvegicus] | 0.5963 | 0.01484368 |
| gi\|83816939 | alpha-1-inhibitor III [Rattus norvegicus] | 0.5976 | 0.0008084 |
| gi\|6981576 | serine protease inhibitor 2b [Rattus norvegicus] | 0.6383 | 0.00603066 |
| gi\|6978515 | apolipoprotein A-I [Rattus norvegicus] | 0.6422 | 0.00111637 |
| gi\|61556986 | transferrin [Rattus norvegicus] | 0.6465 | 5.7019E−10 |
| gi\|50355947 | lamin A isoform C2 [Rattus norvegicus] | 1.2828 | 0.04126772 |
| gi\|31542401 | creatine kinase, brain [Rattus norvegicus] | 1.2924 | 0.02160082 |
| gi\|16923958 | peroxiredoxin 1 [Rattus norvegicus] | 1.3790 | 0.01324064 |
| gi\|62177108 | hypothetical protein LOC298795 [Rattus norvegicus] | 1.3833 | 0.00547971 |
| gi\|158517925 | lectin, galactose binding, soluble 7 [Rattus norvegicus] | 1.3881 | 0.05019835 |
| gi\|109509939 | PREDICTED: similar to Collagen alpha-1(VI) chain precu | 1.4249 | 0.02081841 |
| gi\|11968064 | parvalbumin [Rattus norvegicus] | 1.5826 | 9.5076E−09 |
| gi\|56711254 | procollagen, type III, alpha 1 [Rattus norvegicus] | 1.6331 | 3.8886E−06 |
| gi\|158711704 | collagen, type 1, alpha 1 [Rattus norvegicus] | 1.7477 | 1.7774E−14 |
| gi\|16758080 | procollagen, type I, alpha 2 [Rattus norvegicus] | 1.9007 | 2.8456E−08 |
| gi\|109467089 | PREDICTED: similar to filaggrin [Rattus norvegicus] | 1.9949 | 1.6553E−09 |

REFERENCES

Barrie, K. A., Steinmann, S. P., Shin, A. Y., Spinner, R. J., and Bishop, A. T. Gracilis free muscle transfer for restoration of function after complete brachial plexus avulsion. Neurosurg. Focus 16, 2004. p E8.

Brody, E. N., and Gold, L. Aptamers as therapeutic and diagnostic agents. Rev Molec Biotech. 74, 2000. p 5-13.

Bustin, M. At the crossroads of necrosis and apoptosis: Signaling to multiple cellular targets by HMGB1. Sci. STKE. 151, 2001. p 39.

Gerland, L-M., Peyrol, S., Lallemand, C., Branche, R., Magaud, J. P., Ffrench, M. Association of increased autophagic inclusions labeled for B-galactosidase with fibroblastic aging. Exp. Gerontol. 38, 2003. p 887-895.

Jabloski, E., Adams, T., "The merging of nucleic acid detection and immunoassays" IVD Technology, 12(9), 2006. p 63-70.

Jackson, D. M., The diagnosis of the depth of burning. Br J. Surg. 40, 1953. p 588-596.

Molnar, J. A. MD, PhD, FACS, Jordan L. Simpson, BS, Denise M. Voignier, CMA, Michael J. Morykwas, PhD, and Louis C. Argenta, MD, "Management of an Acute Thermal Injury With Subatmospheric Pressure, J Burns Wounds 4, 2005. p e5.

Mir, M., Katakis, I., and Vreeke, M. Aptamer biosensors: an alternative to immunosensors. IVD Technol. 13(4), 2007. p 39-47.

Parekh, D. Laparoscopic-assisted pancreatic necrosectomy. Arch. Surg. 141, 2006. p 895-903.

Toms, S. A. et al. 2005, in Proceedings, Optical Methods in Drug Discovery and Development. Mostafa Analoui and David A. Dunn, Ed.

Van Herreweghe, F. et al. Proc. Natl. Acad. Sci. USA 99, 2002. p. 949-954.

U.S. Pat. No. 6,057,096.
U.S. Pat. No. 6,174,291.
U.S. Pat. No. 7,052,854.
U.S. Pat. No. 7,149,567.
U.S. Pat. No. 7,366,365.
U.S. Patent Application Publication US 2007/0038121.
U.S. Patent Application Publication US 2007/0197895.
U.S. Patent Application Publication US 2008/0192248.
PCT Publication WO07130423A2.
PCT Publication WO07069040A2.

It should be apparent from the foregoing that an invention having significant advantages has been provided. While the invention is shown in only a few of its forms, it is not just limited to those forms but is susceptible to various changes and modifications without departing from the spirit thereof.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

We claim:

1. A method of determining the viability of a cell in a tissue site, the method comprising:

placing a solid sheet on the tissue site, the solid sheet comprising a compound configured for binding or reacting to a molecule secreted by nonviable tissue on the tissue site; and determining whether the molecule is bound or has reacted to the compound, wherein areas of the sheet comprising the molecule bound to the compound are indicative of nonviable tissue.

2. The method of claim 1, wherein the sheet is a polyhydroxyalkanoate.

3. The method of claim 1, wherein the compound identifies a molecule that is depleted during cell death.

4. The method of claim 1, wherein the compound comprises a dye capable of reacting with said molecule.

5. The method of claim 1, wherein the molecule is a metabolite that is released from nonviable cells more than from viable cells.

6. The method of claim 5, wherein the metabolite is selected from the group consisting of ATP, glucose, glycerol, NADPH and NADH.

7. The method of claim 1, wherein the compound is selected from the group consisting of luciferase, luciferin, glucose oxidase, peroxidase, glycerol kinase, glycerol phosphate oxidase, alcohol dehydrogenase, a tetrazolium dye, phenazine methosulfate, ethidium bromide, and phenazine methosulfate.

8. The method of claim 1, wherein the molecule is a nucleic acid.

9. The method of claim 1, further comprising selectively debriding identified nonviable tissue.

10. The method of claim 1, wherein the sheet is a starch film.

11. The method of claim 1, wherein the sheet is a poly(D,L-lactide-co-glycolide).

12. The method of claim 1, wherein the sheet is a polyglycolic acid.

13. The method of claim 1, wherein the sheet is a poly-(L-lactic acid).

\* \* \* \* \*